(12) United States Patent
Busch et al.

(10) Patent No.: US 7,021,129 B2
(45) Date of Patent: Apr. 4, 2006

(54) DEVICE AND METHOD FOR DETERMINING THE STATE OF AGING OF AN EXHAUST-GAS CATALYTIC CONVERTER

(75) Inventors: Michael-Rainer Busch, Ebersbach (DE); Axel Hirschmann, Goeppingen (DE)

(73) Assignee: DaimlerChrysler AG, Stuttgart (DE)

( * ) Notice: Subject to any disclaimer, the term of this patent is extended or adjusted under 35 U.S.C. 154(b) by 0 days.

(21) Appl. No.: 10/686,810

(22) Filed: Oct. 17, 2003

(65) Prior Publication Data

US 2004/0255655 A1 Dec. 23, 2004

(30) Foreign Application Priority Data

Oct. 19, 2002 (DE) .......................................... 102 48 842

(51) Int. Cl.
*G01M 15/00* (2006.01)

(52) U.S. Cl. ...................................... 73/118.1; 73/23.31

(58) Field of Classification Search ................. 73/23.31, 73/23.32, 112, 116, 117.2, 117.3, 118.1, 119 R
See application file for complete search history.

(56) References Cited

U.S. PATENT DOCUMENTS

| 5,303,580 A | 4/1994 | Schneider et al. .......... 73/118.1 |
| 2003/0005746 A1 * | 1/2003 | Iwazaki et al. ............... 73/1.06 |

FOREIGN PATENT DOCUMENTS

DE 41 12 479 C2 6/2002

* cited by examiner

*Primary Examiner*—Eric S. McCall
(74) *Attorney, Agent, or Firm*—Crowell & Moring LLP

(57) ABSTRACT

Device and method for determining the state of ageing of an exhaust-gas catalytic converter wherein an oxygen sensor having an oxygen-sensitive region and a temperature-sensitive region can be actuated in such a manner that a temperature measurement and, as an alternative, an oxygen partial pressure measurement can be carried out. There is provision for an electrical conductivity of a conductor structure of the oxygen sensor to be determined and for an exhaust-gas temperature to be determined therefrom. From the sensor measurements, the extent of exhaust gas catalytic converter ageing may be assessed.

32 Claims, 5 Drawing Sheets

DEVICE AND METHOD FOR DETERMINING THE STATE OF AGING OF AN EXHAUST-GAS CATALYTIC CONVERTER

This application claims the priority of German patent application 102 48 842.8, filed Oct. 19, 2002, the disclosure of which is expressly incorporated by reference herein.

BACKGROUND AND SUMMARY OF THE INVENTION

The invention relates to a device for determining the state of ageing of an exhaust-gas catalytic converter, and to a method used for this purpose.

German Patent DE 41 12 479 C2 (corresponding to U.S. Pat. No. 5,303,580) describes a method in which the state of ageing of an exhaust-gas catalytic converter is determined with the aid of an oxygen sensor connected to an electronic control unit. The sensor has an oxygen-sensitive region for measuring the oxygen partial pressure in the exhaust gas. The state of ageing of the catalytic converter is determined by the control unit by means of this measured variable.

By contrast, it is an object of the invention to provide a device and a method which allow reliable determination of the state of ageing of an exhaust-gas catalytic converter using simple apparatus.

According to the invention, this object is achieved by a device having an oxygen sensor which is arranged in the exhaust pipe and is assigned to the exhaust-gas catalytic converter, the oxygen sensor having an oxygen-sensitive region for measuring an oxygen partial pressure in the exhaust gas and being connected to an electronic control unit, characterized in that the oxygen sensor has a temperature-sensitive region and can be actuated by the control unit in such a manner that a temperature measurement and/or an oxygen partial pressure measurement can be carried out.

The device according to the invention is distinguished by the fact that the oxygen sensor has a temperature-sensitive region and can be actuated by the control unit in such a manner that a temperature measurement and, as an alternative, the oxygen partial pressure measurement can be carried out. The temperature-sensitive region is in this case at least partially in contact with the exhaust gas. The extent of release of heat of reaction brought about by the catalytic converter can be determined by means of the temperature measurement. Furthermore, the sensor, via the oxygen-sensitive region, can determine the change in the oxygen content in the exhaust gas which is brought about by the catalytic converter. The determination of the two measured variables, temperature and oxygen content, can be carried out as alternatives. It is preferable for the temperature measurement to be carried out when the internal combustion engine is warming up and for the oxygen partial pressure measurement to be carried out when the internal combustion engine has warmed up. The two measured variables are characteristic of various performance features of the catalytic converter, so that its performance and state of ageing can be conclusively ascertained. With regard to the determination of the state of ageing of the catalytic converter, the temperature measurement is preferably used to determine the light-off temperature of the catalytic converter. In the present context, the term light-off temperature is understood, as is customary, to mean the temperature at which the catalytic converter reaches a significant catalytic activity, for example 50% conversion. A low light-off temperature is generally desirable, but this may rise over the course of time during which the catalytic converter is used as a result of ageing. The measurement of the oxygen partial pressure is preferably used to determine the oxygen storage capacity of the catalytic converter. The oxygen storage capacity is likewise subject to ageing. Since the invention allows both the light-off temperature and the oxygen storage capacity of the catalytic converter to be determined, the state of ageing of the catalytic converter can be determined comprehensively and reliably. Furthermore, the measurement of the oxygen partial pressure is used to control the air/fuel ratio ($\lambda$) of the air/fuel mixture supplied to the internal combustion engine. Therefore, the oxygen sensor performs a dual function, so that the device can be of simple design.

In one embodiment of the invention, the temperature-sensitive region of the oxygen sensor is formed by its oxygen-sensitive region and is designed in particular as a solid electrolyte. With this configuration, the invention can be realized by means of an electrochemical sensor. The solid electrolyte is used on the one hand to measure the temperature and on the other hand, as an alternative, to measure the oxygen partial pressure in the exhaust gas, with the same sensor part being used for both jobs. It is preferable for the electrical conductivity of the solid electrolyte to be evaluated in order to measure the temperature and for the electromotive force of the Nernst voltage of the solid electrolyte to be evaluated for the purpose of measuring the oxygen partial pressure. This dual function of the solid electrolyte or the oxygen-sensitive region makes it possible to dispense with additional sensor components, resulting in a simple design of sensor.

In a further embodiment of the invention, the temperature-sensitive region of the oxygen sensor is designed as a heating conductor structure. In this way, the heating conductor structure which is generally already present in an oxygen sensor is advantageously used to measure the temperature. It is preferable for the electrical conductivity of this heating conductor structure to be used for the temperature measurement. For this purpose, the material used for the heating conductor structure can be a material which has a relatively high temperature coefficient of its electrical conductivity, so that a substantial measuring effect is achieved. With this configuration of the invention, it is likewise possible to dispense with additional sensor components and a simple design of sensor likewise results.

In a further embodiment of the invention, a temperature probe is provided in the exhaust pipe, and the temperature probe and the oxygen sensor are arranged in such a manner in the exhaust pipe that at least a partial region of the exhaust-gas catalytic converter is located between the oxygen sensor and the temperature probe. This makes it possible to measure a local temperature difference, so that the amount of heat release caused by exothermic reactions in the catalytic converter region can be determined particularly reliably. Consequently, it is also possible for the light-off temperature of the catalytic converter and/or its ageing-induced deterioration to be determined with particular reliability.

In a further embodiment of the invention, the oxygen sensor is arranged in the exhaust-gas catalytic converter or in the exhaust pipe downstream of the exhaust-gas catalytic converter, and a second oxygen sensor is arranged in the exhaust pipe upstream of the exhaust-gas catalytic converter. This makes it possible to measure a local difference in the oxygen partial pressure in the exhaust gas, so that the oxygen storage capacity of the catalytic converter and/or its ageing-induced deterioration can be determined reliably.

The method according to the invention is distinguished by the fact that as the internal combustion engine is warming up, the electrical conductivity of a conductor structure of the oxygen sensor is measured, a first exhaust-gas temperature is determined from this measurement, and the first exhaust-gas temperature is compared with a second exhaust-gas temperature. A component of the sensor which is of relevance to the measurement of the oxygen partial pressure is preferably used to determine the first exhaust-gas temperature. The exhaust-gas temperature measurement carried out by means of this sensor component and the comparison with a second exhaust-gas temperature make it possible to determine the light-off temperature of the catalytic converter. The second exhaust-gas temperature is therefore preferably a temperature which takes account of the increase in temperature of the exhaust gas as a result of the catalytic converter lighting off. Since the light-off temperature represents an important performance feature of the catalytic converter, its state of ageing can be determined with regard to its ability to catalyse a reaction at an early time. The state of ageing of the catalytic converter which is characterized by the light-off temperature can be expressed, for example, by an ageing characteristic value. After the internal combustion engine has warmed up or after the light-off temperature of the catalytic converter has been determined, it is preferable for the oxygen sensor to be used to measure the oxygen partial pressure of the internal combustion engine exhaust gas. $\lambda$-control for normal operation of the internal combustion engine can then be effected using this measurement.

In one embodiment of the method, to determine the first exhaust-gas temperature the electrical conductivity of a solid electrolyte, which is used to measure the oxygen partial pressure, of the oxygen sensor is measured. This advantageously makes dual use of the sensitive region of the oxygen sensor.

In a further embodiment of the method, to determine the first exhaust-gas temperature the electrical conductivity of a heating conductor structure of the oxygen sensor is measured. Since heating of the oxygen sensor is required for the oxygen partial pressure measurement function, the oxygen sensor is generally provided with a heating conductor structure. Dual use is advantageously made of this component of the oxygen sensor. It is preferable for the temperature to be determined by measuring the conductivity of the heating conductor structure as the internal combustion engine warms up. After it has warmed up or after light-off of the catalytic converter has been determined by means of the temperature determination, operation of the oxygen sensor is switched over to oxygen partial pressure measurement.

In a further embodiment of the method, the second exhaust-gas temperature is measured using a temperature probe arranged in the exhaust pipe. With a suitable arrangement of oxygen sensor and temperature probe, it is possible to record and determine an increase in the exhaust-gas temperature which is brought about by the catalytic converter lighting off. It is therefore likewise possible to conclude whether or not the catalytic converter is lighting off late as a result of ageing and to evaluate the level of catalytic converter ageing with regard to the light-off temperature.

In a further embodiment of the method, the second exhaust-gas temperature is measured using a second oxygen sensor. For this purpose, the second oxygen sensor is actuated as described above, and the second exhaust-gas temperature is measured by measuring the conductivity of its oxygen-sensitive region or its heating conductor structure. It is preferable for the second oxygen sensor to be arranged in the exhaust pipe upstream of the exhaust-gas catalytic converter and for the other oxygen sensor to be arranged in the catalytic converter or in the exhaust pipe downstream of the catalytic converter. After light-off of the catalytic converter has been recorded, the oxygen sensors are used to measure the oxygen partial pressure and they can be used, for example, to perform $\lambda$-control.

In a further embodiment of the method, the second exhaust-gas temperature is determined by modelling. By way of example, expected values for an exhaust-gas temperature at the location of the oxygen sensor can be stored in a control unit by comparison measurements with an unaged catalytic converter. In this case, it is possible also to take into account the operating point of the internal combustion engine. Conclusions can be drawn as to the light-off temperature and/or the state of ageing of the catalytic converter by comparison with the first exhaust-gas temperature determined using the oxygen sensor.

In a further embodiment of the method, a light-off temperature of the catalytic converter is determined from the comparison of the first exhaust-gas temperature and the second exhaust-gas temperature, and an oxygen storage capacity of the catalytic converter is determined from the measurement of the oxygen partial pressure, and the state of ageing of the catalytic converter is determined from the light-off temperature and the oxygen storage capacity. By way of example, the state of ageing of the catalytic converter, as characterized by the light-off temperature, can be expressed by a first ageing characteristic value, and the state of ageing of the catalytic converter, as characterized by the oxygen storage capacity, can be expressed by a second ageing characteristic value. The ageing characteristic values can then be levelled out or compared with one another, so that the state of ageing of the catalytic converter can be analysed more reliably and more comprehensively.

Other objects, advantages and novel features of the present invention will become apparent from the following detailed description of the invention when considered in conjunction with the accompanying drawings.

DETAILED DESCRIPTION OF THE DRAWINGS

Figure 1:
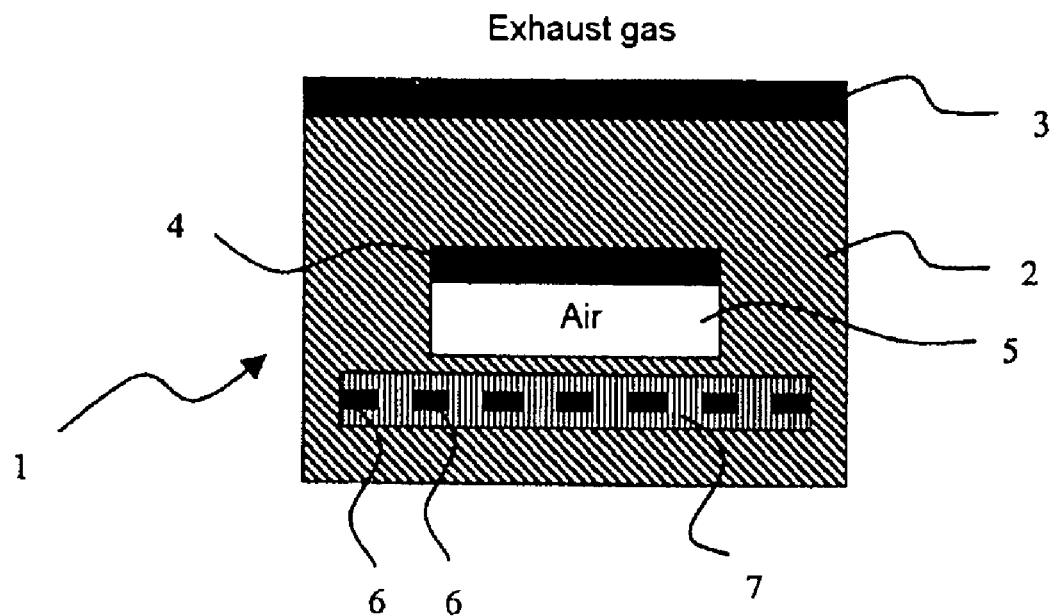
FIG. 1 shows a diagrammatically depicted cross section through an oxygen sensor.

FIG. 1 diagrammatically depicts a cross section through the structure of an electrochemical oxygen sensor 1. The oxygen sensor 1 has an oxygen-sensitive region 2 which is formed, for example, by a solid electrolyte which contains zirconium dioxide ($ZrO_2$) and has an oxygen conductivity. The oxygen-sensitive region 2 on one side has a phase boundary with respect to the exhaust-gas side and on the other side has a phase boundary with respect to the air side. An exhaust-gas electrode 3 and an air electrode 4 are arranged on the solid electrolyte at these phase boundaries. The electrodes 3, 4 are gas-permeable, so that contact between the corresponding gas and the solid electrolyte is possible. Moreover, the oxygen sensor 1 has a heating conductor structure 6 which is embedded in an insulator 7 and is in thermal contact with the oxygen-sensitive region 2. The electrical feed lines which are required to operate the sensor 1 and a connected control unit are not illustrated, for the sake of clarity.

To measure the oxygen partial pressure in the exhaust gas, the sensor 1 is heated to its operating temperature by current being supplied to the heating conductor structure 6. Oxidation or reduction reactions, which lead to a thermodynamic equilibrium being established with regard to the oxygen partial pressure, may occur at the exhaust-gas electrode 3. Designing the exhaust-gas electrode 3 to contain precious metal makes it possible to catalytically assist this operation. Differences between the oxygen partial pressure on the exhaust-gas side and the known oxygen partial pressure on the air side manifest themselves in the occurrence of a Nernst voltage which can be tapped off at the electrodes 3, 4. The oxygen sensor 1 can in this case be considered an active component in the electrical engineering sense. The Nernst voltage is determined and evaluated by the connected control unit, so that the oxygen partial pressure in the exhaust gas is measured.

This function of the electrochemical oxygen sensor 1, which is known per se, is now supplemented according to the invention by a temperature-measuring function. To carry out this function, the heating remains switched off and a test voltage is applied to the electrodes 3, 4, and the level of current flowing is measured. This is used to determine the electrical conductivity of the oxygen-sensitive region 2. The oxygen sensor 1 can in this case be considered a passive component in the electrical engineering sense. The electrical conductivity of the solid electrolyte has a material-specific temperature dependency which is available to the connected control unit for analysis. Therefore, the temperature of the solid electrolyte can easily be determined in the control unit using the electrical conductivity value. The oxygen-sensitive region 2 of the oxygen sensor 1 therefore serves as a temperature-sensitive region when the sensor is performing this function. Since the oxygen sensor is in contact with the exhaust gas, the solid electrolyte of the sensor 1 approximately adopts the exhaust-gas temperature, and consequently the exhaust-gas temperature can also be determined from the temperature of the solid electrolyte. Any temperature losses which may be present at the phase boundary and in the temperature-sensitive region 2 can be taken into account by advance calibration of the sensor which takes such losses into account. It is preferable for the control unit to contain a characteristic curve which describes the relationship between the electrical conductivity of the temperature-sensitive region 2 and the exhaust-gas temperature and which is evaluated by the control unit.

The heating conductor structure 6 can in a similar way likewise act as a temperature-sensitive region and be used to determine the exhaust-gas temperature. For this purpose, a test voltage is likewise applied to the terminals of the heating conductor structure 6, and the flow of current is measured. The electrical conductivity of the heating conductor structure 6 is determined from the magnitude of the test voltage and the level of the current flowing. The exhaust-gas temperature is then determined analogously to the procedure described above.

It is advantageous in particular for the exhaust-gas temperature to be determined both via the electrical conductivity of the solid electrolyte and via the electrical conductivity of the heating conductor structure 6. In this operating mode of the oxygen sensor 1, the solid electrolyte and the heating conductor structure 6 each form a temperature-sensitive region. Therefore, two measured values, which can be compared with one another and/or levelled out, are obtained for the exhaust-gas temperature. This increases the accuracy of the determination of the temperature of the exhaust gas. The accuracy can be further improved by taking account of the air temperature. For this purpose, the latter temperature is determined, for example by a temperature sensor (not shown), and is used for correction purposes when determining the exhaust-gas temperature.

The text which follows explains various arrangements of an exhaust-gas catalytic converter and an oxygen sensor which can be used to determine the state of ageing of the exhaust-gas catalytic converter.

Figure 2:
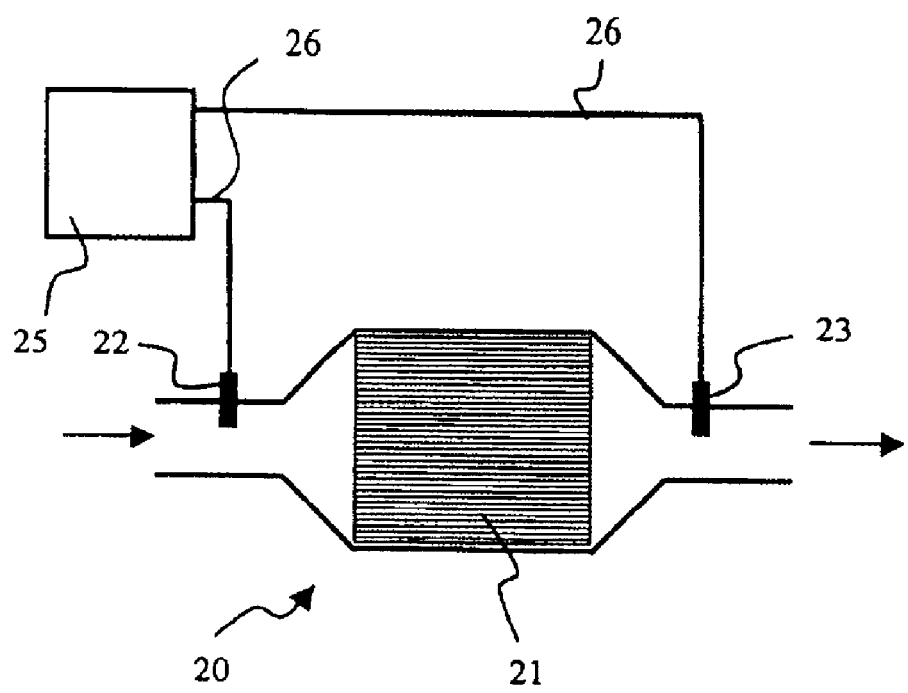
FIG. 2 shows a schematic block diagram of an arrangement of oxygen sensors and an exhaust-gas catalytic converter.

FIG. 2 shows a catalytic converter 20 which is arranged in an exhaust pipe of an internal combustion engine (not shown), preferably close to the internal combustion engine. An exhaust-gas catalytic converter 21 with an oxygen storage capacity, such as for example a three-way catalytic converter or an oxidation catalytic converter, is provided in the catalytic converter 20. The direction of flow of the exhaust gas is indicated by arrows. An oxygen sensor 22 and 23 is arranged in the exhaust pipe on the inlet side and the outlet side, respectively, of the exhaust-gas catalytic converter 21. The sensors 22, 23 are connected to a control unit 25 via control lines 26. The oxygen sensor 23 is designed as described in connection with FIG. 1 and can be actuated and operated by the control unit 25 both to determine the oxygen partial pressure in the exhaust gas and to determine the exhaust-gas temperature, as described. The oxygen sensor 22 can be of any desired design.

To determine the state of ageing of the catalytic converter 21, its light-off temperature and its oxygen storage capacity are determined as described below.

After the internal combustion engine has started up, the oxygen sensor 23, as described above, is operated in a first mode for temperature measurement. The first exhaust-gas temperature determined in this way downstream of the catalytic converter is compared by the control unit 25 with a second exhaust-gas temperature which is to be expected at the location of the oxygen sensor 23. The expected second exhaust-gas temperature in this case results from a calculation model or from characteristic diagrams which are available to the control unit 25. The starting point in this case is advantageously an exhaust-gas temperature on the entry side of the catalytic converter 21, which has been modelled on the basis of the operating parameters of the internal combustion engine. The model or the characteristic diagrams also take into account the fact that additional introduction of heat into the exhaust gas takes place at a predeterminable time as a result of the unaged catalytic converter 21 lighting off. If the first exhaust-gas temperature determined by means of the oxygen sensor remains behind the modelled second exhaust-gas temperature in terms of its magnitude and/or in terms of time, this can be attributed to an increased light-off temperature induced by ageing. Consequently, the state of ageing of the catalytic converter 21 can be analysed with regard to its light-off temperature by comparison of the first exhaust-gas temperature, determined by means of the oxygen sensor 23, with the modelled second exhaust-gas temperature. In the event of a suitably high deterioration in the light-off temperature, the control unit 25 can output a signal which indicates the increased catalytic converter ageing.

When the internal combustion engine has warmed up or after a predeterminable exhaust-gas temperature has been reached, the oxygen sensors are used for λ-control of the internal combustion engine. In this case, the oxygen sensor 22 serves as a control sensor, and the oxygen sensor 23 serves as a trimming sensor or a diagnosis sensor. With the aid of the oxygen sensor 22, a λ-control oscillation of defined amplitude and frequency at which the combustion operations in the internal combustion engine take place is imposed. The procedure for doing this will be familiar to the person skilled in the art and requires no further explanation at this point. The λ-oscillations in the exhaust-gas composition which are present on the entry side of the catalytic converter 21, however, are increasingly smoothed as the exhaust gas passes through the catalytic converter, on account of its oxygen storage capacity. The result is a decrease in the amplitude of the λ-oscillation across the catalytic converter. With a high oxygen storage capacity, by way of example, it is no longer possible to detect any λ-oscillation on the exit side of the catalytic converter 21. In this case, the λ value has levelled out at the constant mean value of the λ-oscillation present upstream of the catalytic converter 21. The amplitude of the λ-oscillation which can be detected after the exhaust gas has passed through a partial section of or the entire catalytic converter 21 is therefore a measure of the oxygen storage capacity of the catalytic converter partial section or of the entire catalytic converter 21. In chemical equilibrium, however, the λ value is derived directly from the oxygen partial pressure. Therefore, by measuring the oxygen partial pressure using the oxygen sensor 23, it is possible to determine the λ value at the installation site and therefore also to determine the oxygen storage capacity of the catalytic converter 21. To be more precise, it should be mentioned that the oxygen storage capacity of the catalytic converter 21 can be determined in particular when a detectable amplitude of the λ-oscillation is present. If no such amplitude is present, it is generally only possible to conclude that the oxygen storage capacity of the catalytic converter 21 has not dropped below a defined level. In this case, it can be assumed that the catalytic converter 21 has not undergone any ageing in terms of its oxygen storage capacity.

If the oxygen sensor 23 on the exit side of the catalytic converter 21 records some degree of amplitude of the λ-oscillation, this means that some degree of catalytic converter ageing has occurred. Therefore, the catalytic converter ageing can be determined in the manner outlined by measurement of the oxygen storage capacity. This operating mode of the oxygen sensor 23 is set after the internal combustion engine has warmed up or after light-off of the catalytic converter 21 has been recorded. For this purpose, the oxygen sensor 23 has to be heated to operating temperature by passing current through the heating conductor structure 6. This makes it available for measurement of the oxygen partial pressure. Temperature determination by means of the oxygen sensor 23 is now no longer desired.

Figure 3:
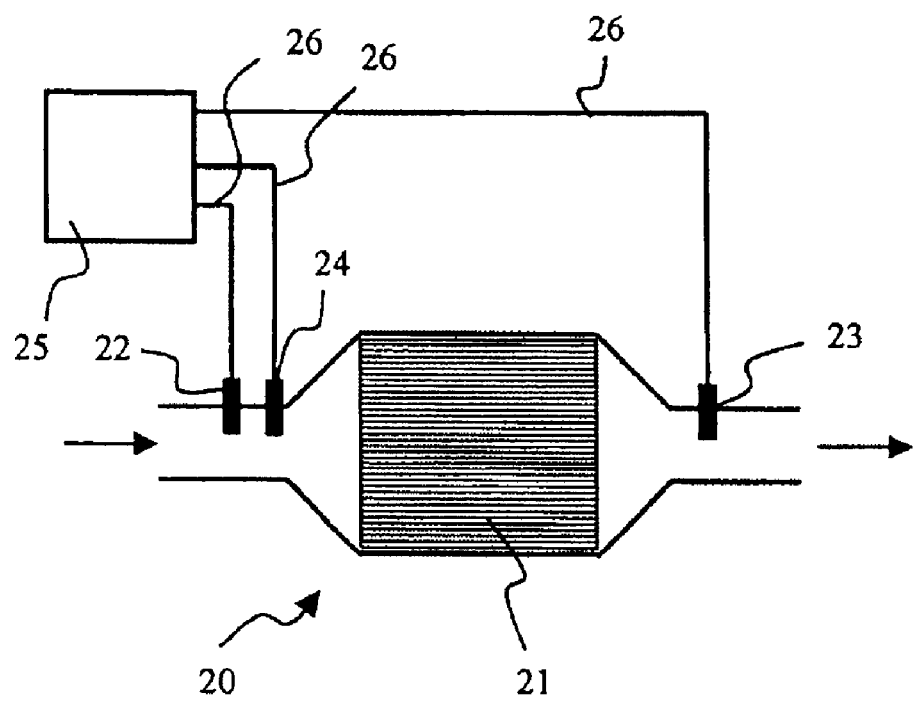
FIG. 3 shows a schematic block diagram of a second arrangement of oxygen sensors and an exhaust-gas catalytic converter.

FIG. 3 shows a further advantageous arrangement for realizing the invention. Components which have substantially the same effect in this figure and in the following figures are denoted by the same reference numerals as in FIG. 2. Unlike in the arrangement shown in FIG. 2, in this case a temperature probe 24 is additionally provided in the exhaust pipe on the entry side of the catalytic converter 21. The temperature probe 24 is likewise connected to the control unit 25 via a control line 26.

Analogously to the procedure corresponding to the arrangement shown in FIG. 2, the state of ageing of the catalytic converter is assessed with regard to its light-off temperature by comparing the first exhaust-gas temperature, determined by means of the oxygen sensor 23, with the modelled second exhaust-gas temperature. The light-off of the catalytic converter 21 can also be monitored directly by forming the difference between the first exhaust-gas temperature, determined by means of the oxygen sensor 23, and the exhaust-gas temperature determined by means of the temperature probe 24. If a temperature difference does not occur to the same extent, and/or occurs at a later time, compared to the temperature difference which would be expected in an unaged catalytic converter 21, an ageing-induced deterioration in the catalytic converter action is observed and is evaluated accordingly. Of course, it is also possible to determine ageing of the catalytic converter 21 with regard to its oxygen storage capacity, as in the arrangement illustrated in FIG. 2, and this step is carried out after the internal combustion engine has warmed up or after a predeterminable exhaust-gas temperature has been reached, as described. The same also applies to the λ-control of the internal combustion engine operation. With this temperature probe 24, the exhaust-gas temperature upstream of the catalytic converter 21 can be determined more accurately than by modelling. Therefore, the modelling of the exhaust-gas temperature on the exit side of the catalytic converter leads to a more accurate and more reliable result.

Figure 4:
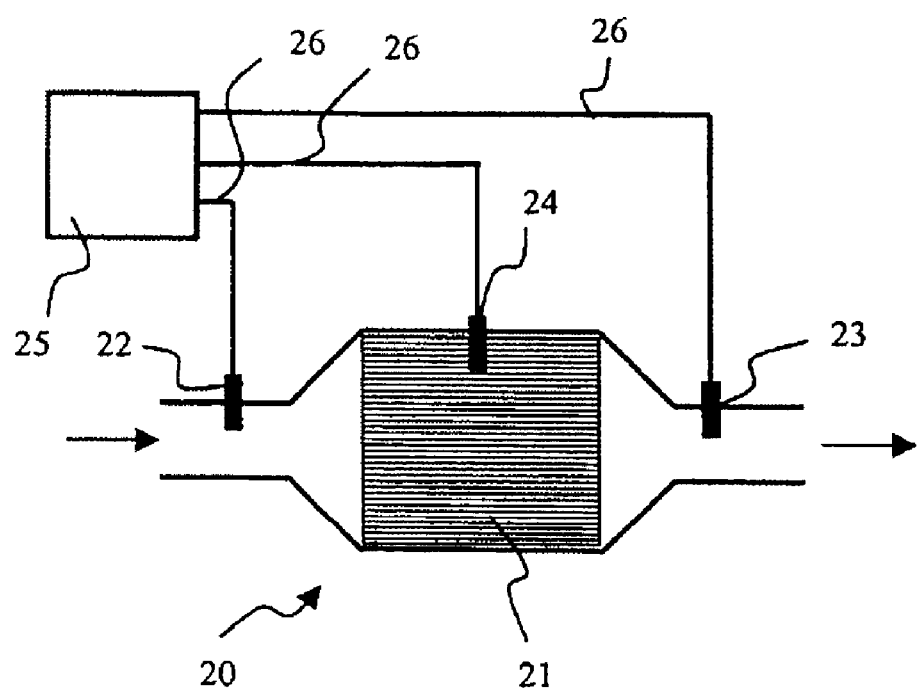
FIG. 4 shows a schematic block diagram of a third arrangement of oxygen sensors and an exhaust-gas catalytic converter.

FIG. 4 shows a further advantageous arrangement used to implement the invention. Unlike in FIG. 3, the temperature probe 24 or its temperature-sensitive part is arranged in the catalytic converter 21. The procedure used to determine the catalytic converter ageing to a very large extent corresponds to the procedure which has been explained in connection with the arrangement shown in FIG. 3. Furthermore, the arrangement shown in FIG. 4 makes it possible specifically to analyse the catalytic converter part located downstream of the temperature sensor 24. Exothermic reactions which occur in this downstream catalytic converter part can be recorded using this arrangement by measuring the temperature difference. If such reactions are recorded, this is an indication of catalytic converter ageing, since in an unaged catalytic converter the reactions take place primarily in the upstream region. However, on account of the thermal loading, catalytic converter ageing also occurs earlier in the upstream region of the catalytic converter 21. Therefore, with the arrangement shown in FIG. 4, it is possible to reliably recognize catalytic converter ageing with regard to the light-off temperature. Determination of ageing of the catalytic converter 21 with regard to its oxygen storage capacity and λ-control of the internal combustion engine operation are carried out in the same way as described above.

Figure 5:
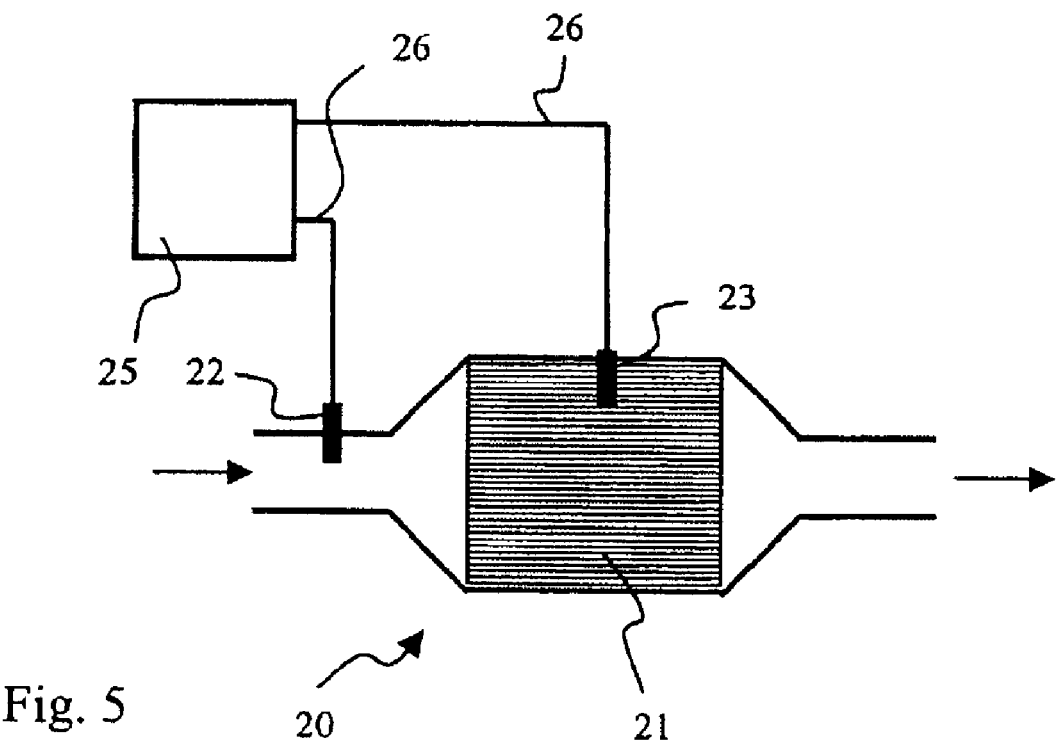
FIG. 5 shows a schematic block diagram of a fourth arrangement of oxygen sensors and an exhaust-gas catalytic converter.

FIG. 5 shows a further advantageous arrangement for realizing the invention. Unlike in the arrangement illustrated in FIG. 2, in this case the oxygen sensor 23 or its temperature-sensitive region is arranged in the catalytic converter 21. The catalytic converter ageing is determined analogously to the arrangement illustrated in FIG. 2. However, by determining the temperature in the catalytic converter 21, it is possible to evaluate the efficiency of the catalytic converter part upstream of the oxygen sensor 23 more accurately. Since ageing phenomena preferentially occur in the upstream region of the catalytic converter 21, it is therefore possible to reliably detect catalytic converter ageing with regard to the light-off temperature. The same is also true of the determination of the ageing of the catalytic converter 21 with regard to its oxygen storage capacity, which is carried out as has already been explained above. Since the arrangement of the oxygen sensor 23 in the catalytic converter 21 means that only that part of the catalytic converter which lies upstream of the sensor 23 is recorded, in this case imposed λ-oscillations occur to a greater extent and the determination of the ageing of the catalytic converter 21 with regard to its oxygen storage capacity is more sensitive and more accurate.

Figure 6:
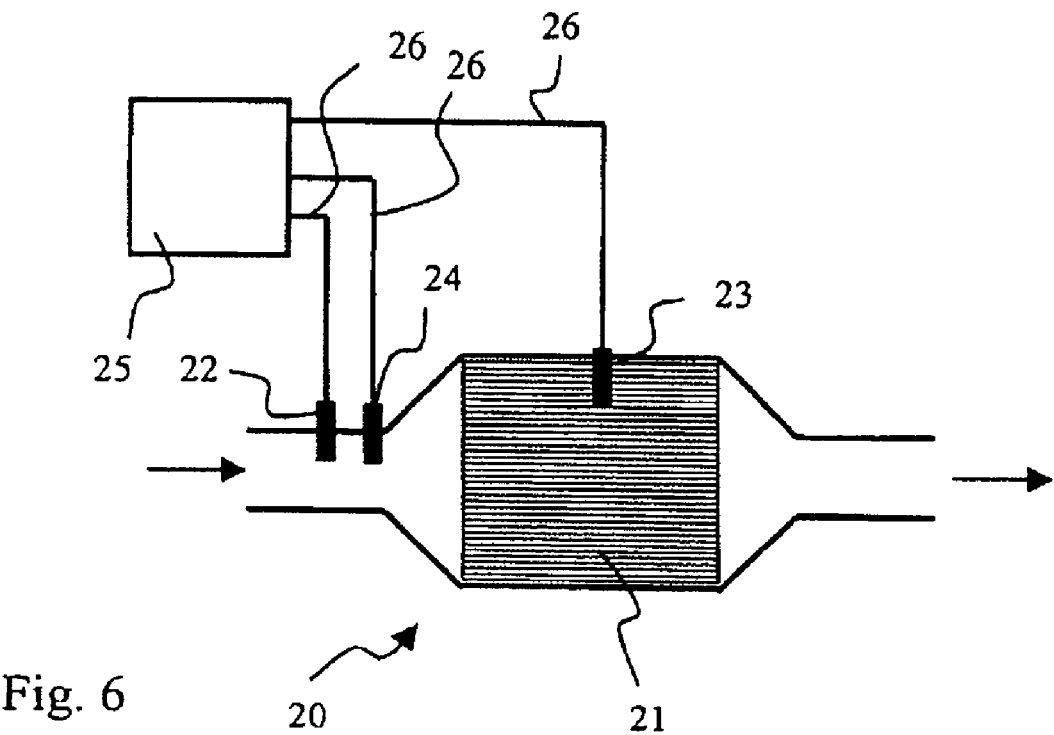
FIG. 6 shows a schematic block diagram of a fifth arrangement of oxygen sensors and an exhaust-gas catalytic converter.

FIG. 6 shows a further advantageous arrangement for realizing the invention. Unlike in FIG. 5, in this case a temperature probe 24 is additionally arranged in the exhaust pipe on the entry side of the catalytic converter 21. This temperature probe 24 allows the exhaust-gas temperature upstream of the catalytic converter 21 to be determined more accurately than by modelling. This leads to a more reliable result when determining the state of ageing of the catalytic converter 21 in accordance with the procedure used in the arrangement illustrated in FIG. 5. With the arrangement shown in FIG. 6, it is possible to directly determine an increase in the exhaust-gas temperature caused by reactions in the upstream part of the catalytic converter by difference measurement. This allows reliable evaluation of the state of ageing of the catalytic converter 21. The ageing of the catalytic converter 21 with regard to its oxygen storage capacity is determined in the same way as in the arrangement illustrated in FIG. 5.

Figure 7:
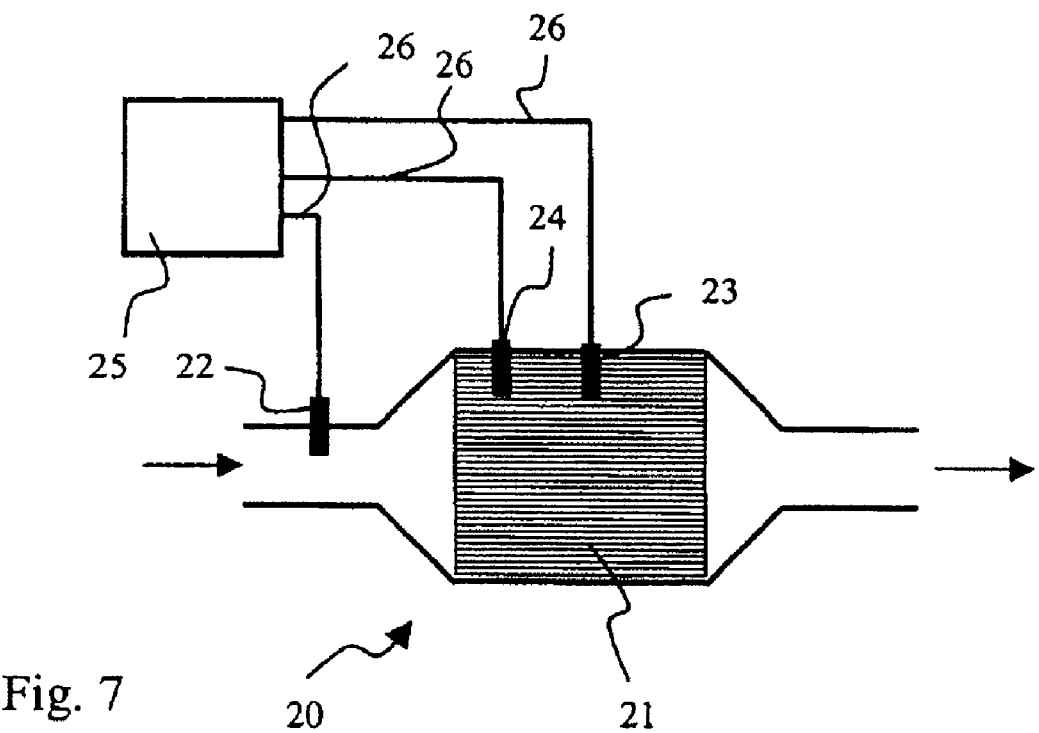
FIG. 7 shows a schematic block diagram of a sixth arrangement of oxygen sensors and an exhaust-gas catalytic converter.

FIG. 7 shows a further advantageous arrangement for realizing the invention. Unlike in the arrangement illustrated in FIG. 6, in this case the temperature probe 24 is arranged in the catalytic converter 21, upstream of the oxygen sensor 23. With this arrangement, it is possible, by means of a temperature difference measurement, to monitor a catalytic converter partial region, preferably in the front half of the catalytic converter 21. The catalytic converter ageing with regard to the light-off temperature of the catalytic converter 21 then relates primarily to this partial region of the catalytic converter. The ageing of the catalytic converter 21 with regard to its oxygen storage capacity is determined in the same way as in the arrangements illustrated in FIGS. 5 and 6.

Figure 8:
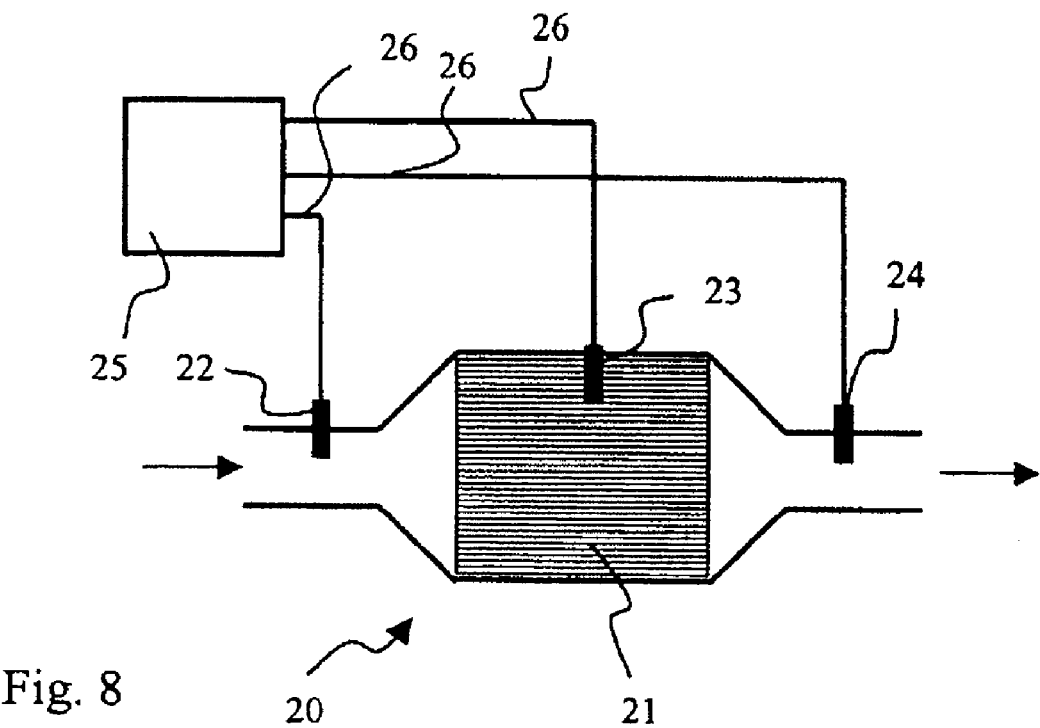
FIG. 8 shows a schematic block diagram of a seventh arrangement of oxygen sensors and an exhaust-gas catalytic converter.

FIG. 8 shows a further advantageous arrangement for realizing the invention. Unlike in the arrangement illustrated in FIG. 7, in this case the temperature probe 24 is arranged in the exhaust pipe on the exit side of the catalytic converter 21 and downstream of the oxygen sensor 23. On the one hand, a temperature difference measurement can be carried out with the aid of the oxygen sensor 23 and the temperature probe 24. In this case, the catalytic converter part lying downstream of the oxygen sensor 23 is evaluated with regard to its catalytic activity. On the other hand, it is possible to work on the basis of an exhaust-gas temperature which is present on the entry side of the catalytic converter 21 and is obtained by modelling as explained above. In this case, the temperature difference determination allows the entire catalytic converter 21 to be evaluated integrally with regard to its catalytic activity and its ageing. The procedure in principle corresponds to that used in the arrangement illustrated in FIG. 4. With regard to the catalytic converter ageing in terms of the oxygen storage capacity, the statements which have been made in connection with the arrangement illustrated in FIG. 7 apply in this case too.

Figure 9:
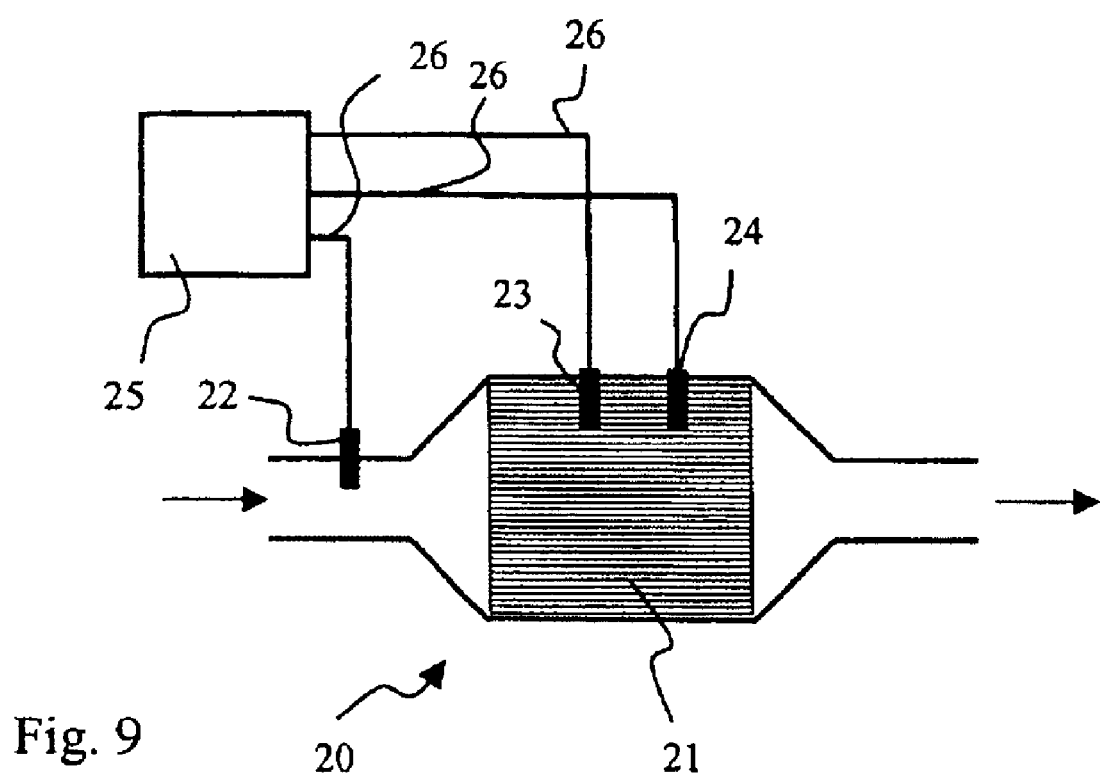
FIG. 9 shows a schematic block diagram of an eighth arrangement of oxygen sensors and an exhaust-gas catalytic converter.

FIG. 9 shows a further advantageous arrangement for realizing the invention. The temperature probe 24 is in this case likewise arranged downstream of the oxygen sensor 23, but unlike in the design illustrated in FIG. 8 is arranged in the downstream region of the catalytic converter 21. The procedure used to determine the catalytic converter ageing largely corresponds to that used in the arrangement shown in FIG. 8. However, on account of the fact that the temperature probe 24 is arranged in the catalytic converter, only the exothermic characteristics of an upstream catalytic converter volume are recorded. Determination of the ageing of the catalytic converter with regard to its oxygen storage capacity takes place as in the arrangements illustrated in FIGS. 5 to 8.

A further improvement to the determination of the catalytic converter ageing with regard to the light-off temperature is achieved by using an oxygen sensor 22 which is of similar construction to the oxygen sensor 23. This is then likewise used to determine the temperature during the warm-up phase of the internal combustion engine. Together with a temperature probe 24 arranged between the oxygen sensors 22, 23, three temperatures determined at different locations are then available. The locations can be selected appropriately with a view to acquiring information which is as accurate as possible, with the oxygen sensor 22 being arranged upstream of the catalytic converter 21 for reasons of λ-control. The oxygen sensor 23 and the temperature probe 24 may be arranged both in the catalytic converter 21 and also in the exhaust pipe on the exit side of the catalytic converter 21. This allows accurate position resolution when determining the activity of the catalytic converter 21 and therefore accurate and reliable determination of its state of ageing. However, if appropriate it is also possible to make do without the temperature probe 24.

As has been explained, the device according to the invention and the method according to the invention can be used to determine and monitor the state of ageing of a catalytic converter both with regard to its light-off temperature and with regard to its oxygen storage capacity. Since two different properties of the catalytic converter are being recorded, and these properties are subject to different ageing influences, this allows comprehensive and reliable evaluation of the catalytic converter ageing. The ageing with regard to the light-off temperature can be evaluated separately from the oxygen storage capacity. By way of example, it is possible to provide for a warning signal to be activated for both properties. It is in each case advantageous to introduce an ageing characteristic value, for example related to a maximum permissible ageing. The two separately determined characteristic values may, however, also be combined to form a common ageing characteristic value, and a signal can be output when a definable level of ageing is exceeded.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the of the appended claims and equivalents thereof.

What is claimed is:

1. An apparatus for monitoring the performance of an exhaust-gas catalytic converter arranged in an exhaust pipe of an internal combustion engine, comprising:
   an oxygen sensor disposed in the exhaust pipe, the oxygen sensor having an oxygen-sensitive region for detecting an oxygen partial pressure in the exhaust gas and a temperature-sensitive region for detecting a temperature of the exhaust gas; and a control unit adapted to receive signals from the oxygen sensor corresponding to a detected oxygen partial pressure and a detected exhaust gas temperature, wherein the control unit has at least two modes, including a first operating mode for operating the oxygen sensor as a temperature sensor which determines the exhaust gas temperature and a second operating mode for determining the oxygen partial pressure of the exhaust gas.

2. The apparatus of claim 1 wherein the control unit determines the exhaust gas temperature in the first operating mode by at least one of determining the electrical conductivity of a solid electrolyte region of the oxygen sensor and determining the electrical conductivity of a heating structure of the oxygen sensor.

3. The apparatus of claim 1 wherein the control unit determines the light-off temperature of the catalytic converter based on the exhaust gas temperature determined in the first operating mode.

4. The apparatus of claim 2 wherein the control unit determines the light-off temperature of the catalytic converter based on the exhaust gas temperature determined in the first operating mode.

5. The apparatus of claim 1 wherein the control unit determines the oxygen storage capacity of the catalytic converter based on the oxygen partial pressure of the exhaust gas determined in the second operating mode.

6. The apparatus of claim 2 wherein the control unit determines the oxygen storage capacity of the catalytic converter based on the oxygen partial pressure of the exhaust gas determined in the second operating mode.

7. The apparatus of claim 3 wherein the control unit determines the oxygen storage capacity of the catalytic converter based on the oxygen partial pressure of the exhaust gas determined in the second operating mode.

8. The apparatus of claim 4 wherein the control unit determines the oxygen storage capacity of the catalytic converter based on the oxygen partial pressure of the exhaust gas determined in the second operating mode.

9. The apparatus of claim 1 further comprising:
a temperature probe provided in the exhaust pipe,
wherein at least a partial region of the catalytic converter is located between the oxygen sensor and the temperature probe.

10. The apparatus of claim 2 further comprising:
a temperature probe provided in the exhaust pipe,
wherein at least a partial region of the catalytic converter is located between the oxygen sensor and the temperature probe.

11. The apparatus of claim 3 further comprising:
a temperature probe provided in the exhaust pipe,
wherein at least a partial region of the catalytic converter is located between the oxygen sensor and the temperature probe.

12. The apparatus of claim 4 further comprising:
a temperature probe provided in the exhaust pipe,
wherein at least a partial region of the catalytic converter is located between the oxygen sensor and the temperature probe.

13. The apparatus of claim 5 further comprising:
a temperature probe provided in the exhaust pipe,
wherein at least a partial region of the catalytic converter is located between the oxygen sensor and the temperature probe.

14. The apparatus of claim 6 further comprising:
a temperature probe provided in the exhaust pipe,
wherein at least a partial region of the catalytic converter is located between the oxygen sensor and the temperature probe.

15. The apparatus of claim 7 further comprising:
a temperature probe provided in the exhaust pipe,
wherein at least a partial region of the catalytic converter is located between the oxygen sensor and the temperature probe.

16. The apparatus of claim 8 further comprising:
a temperature probe provided in the exhaust pipe,
wherein at least a partial region of the catalytic converter is located between the oxygen sensor and the temperature probe.

17. The apparatus of claim 1 further comprising:
a second oxygen sensor disposed in the exhaust pipe upstream of the catalytic converter,
wherein the first oxygen sensor is disposed in one of the catalytic converter and the exhaust gas pipe downstream of the catalytic converter.

18. The apparatus of claim 2 further comprising:
a second oxygen sensor disposed in the exhaust pipe upstream of the catalytic converter,
wherein the first oxygen sensor is disposed in one of the catalytic converter and the exhaust gas pipe downstream of the catalytic converter.

19. The apparatus of claim 3 further comprising:
a second oxygen sensor disposed in the exhaust pipe upstream of the catalytic converter,
wherein the first oxygen sensor is disposed in one of the catalytic converter and the exhaust gas pipe downstream of the catalytic converter.

20. The apparatus of claim 4 further comprising:
a second oxygen sensor disposed in the exhaust pipe upstream of the catalytic converter,
wherein the first oxygen sensor is disposed in one of the catalytic converter and the exhaust gas pipe downstream of the catalytic converter.

21. The apparatus of claim 5 further comprising:
a second oxygen sensor disposed in the exhaust pipe upstream of the catalytic converter,
wherein the first oxygen sensor is disposed in one of the catalytic converter and the exhaust gas pipe downstream of the catalytic converter.

22. The apparatus of claim 6 further comprising:
a second oxygen sensor disposed in the exhaust pipe upstream of the catalytic converter,
wherein the first oxygen sensor is disposed in one of the catalytic converter and the exhaust gas pipe downstream of the catalytic converter.

23. The apparatus of claim 7 further comprising:
a second oxygen sensor disposed in the exhaust pipe upstream of the catalytic converter,
wherein the first oxygen sensor is disposed in one of the catalytic converter and the exhaust gas pipe downstream of the catalytic converter.

24. The apparatus of claim 8 further comprising:
a second oxygen sensor disposed in the exhaust pipe upstream of the catalytic converter,
wherein the first oxygen sensor is disposed in one of the catalytic converter and the exhaust gas pipe downstream of the catalytic converter.

25. The apparatus of claim 9 further comprising:

a second oxygen sensor disposed in the exhaust pipe upstream of the catalytic converter, wherein the first oxygen sensor is disposed in one of the catalytic converter and the exhaust gas pipe downstream of the catalytic converter.

26. The apparatus of claim 10 further comprising:

a second oxygen sensor disposed in the exhaust pipe upstream of the catalytic converter, wherein the first oxygen sensor is disposed in one of the catalytic converter and the exhaust gas pipe downstream of the catalytic converter.

27. The apparatus of claim 11 further comprising:

a second oxygen sensor disposed in the exhaust pipe upstream of the catalytic converter, wherein the first oxygen sensor is disposed in one of the catalytic converter and the exhaust gas pipe downstream of the catalytic converter.

28. The apparatus of claim 12 further comprising:

a second oxygen sensor disposed in the exhaust pipe upstream of the catalytic converter, wherein the first oxygen sensor is disposed in one of the catalytic converter and the exhaust gas pipe downstream of the catalytic converter.

29. The apparatus of claim 13 further comprising:

a second oxygen sensor disposed in the exhaust pipe upstream of the catalytic converter, wherein the first oxygen sensor is disposed in one of the catalytic converter and the exhaust gas pipe downstream of the catalytic converter.

30. The apparatus of claim 14 further comprising:

a second oxygen sensor disposed in the exhaust pipe upstream of the catalytic converter, wherein the first oxygen sensor is disposed in one of the catalytic converter and the exhaust gas pipe downstream of the catalytic converter.

31. The apparatus of claim 15 further comprising:

a second oxygen sensor disposed in the exhaust pipe upstream of the catalytic converter, wherein the first oxygen sensor is disposed in one of the catalytic converter and the exhaust gas pipe downstream of the catalytic converter.

32. The apparatus of claim 16 further comprising:

a second oxygen sensor disposed in the exhaust pipe upstream of the catalytic converter, wherein the first oxygen sensor is disposed in one of the catalytic converter and the exhaust gas pipe downstream of the catalytic converter.

* * * * *